(12) United States Patent
MacDermott et al.

(10) Patent No.: US 7,468,003 B2
(45) Date of Patent: Dec. 23, 2008

(54) PROSTHETIC DEVICE FOR GOLFING

(75) Inventors: Robert MacDermott, Edmonton (CA); Gary Tremblay, Leduc (CA); Randall Berg, Edmonton (CA)

(73) Assignee: Troppman Prosthetics Ltd., Edmonton, Alberta (CA)

( * ) Notice: Subject to any disclaimer, the term of this patent is extended or adjusted under 35 U.S.C. 154(b) by 0 days.

(21) Appl. No.: 11/401,108

(22) Filed: Apr. 10, 2006

(65) Prior Publication Data
US 2007/0105638 A1    May 10, 2007

(51) Int. Cl.
A63B 69/36 (2006.01)
A61F 2/54 (2006.01)

(52) U.S. Cl. .............. 473/210; 473/212; 473/226; 623/61; 623/65

(58) Field of Classification Search .............. 473/201, 473/203, 204–207, 212, 226, 229; 623/33, 623/57–65, 66.1
See application file for complete search history.

(56) References Cited

U.S. PATENT DOCUMENTS

| | | | |
|---|---|---|---|
| 3,747,128 A | 7/1973 | De Filipop | |
| 3,965,491 A | 6/1976 | Frenzel | |
| 4,357,717 A | 11/1982 | Puhl | |
| 4,661,113 A * | 4/1987 | Adkins | 623/65 |
| 4,911,725 A | 3/1990 | Duvieilh | |
| 5,464,444 A * | 11/1995 | Farquharson et al. | 623/65 |
| 6,416,555 B1 * | 7/2002 | Dillenburg et al. | 623/65 |
| 6,485,523 B2 | 11/2002 | Pierce et al. | |
| 6,582,473 B2 | 6/2003 | Pierce et al. | |
| D514,397 S * | 2/2006 | Zellmer et al. | D7/665 |
| 2002/0116073 A1 * | 8/2002 | Pierce et al. | 623/61 |

OTHER PUBLICATIONS

TRS, 'The Amputee Golf Grip and Gof Pro', available at http://www.oandp.com/products/trs/sports-recreation/golf.asp, at least as early as Oct. 2004.

* cited by examiner

Primary Examiner—Nini Legesse
(74) Attorney, Agent, or Firm—Davis Bujold & Daniels, P.L.L.C.

(57) ABSTRACT

A prosthetic device for golfing having an elongate resilient body with an axis, a first end, a second end and an exterior golf club support surface extending along the axis between the first end and the second end. Gripping members are positioned on opposed sides of the golf club support surface adjacent the first end. The gripping members are adapted to grip a golf club shaft and maintain the golf club shaft engaged with the golf club support surface. A coupling is provided at the first end which is adapted to be secured to a terminal device worn by the user. The coupling element may be either a male end or female end attached to the first end.

8 Claims, 3 Drawing Sheets

PROSTHETIC DEVICE FOR GOLFING

This application claims priority from Canadian Application Serial No. 2,525,888 filed Nov. 4, 2005.

FIELD OF THE INVENTION

The present invention relates to a prosthetic device for golfing.

BACKGROUND OF THE INVENTION

Golf is a recreational activity enjoyed by many. It's benefits include social interaction, exercise, as well as the psychological well-being that people get from being outdoors and playing a game they really enjoy. For someone who has lost the ability to enjoy golf due to an upper extremity amputation, the impact on their quality of life can be substantial.

Some adaptive devices have been developed to which enable a person with an upper extremity amputation to hold a golf club such as U.S. Pat. No. 4,911,725 (Duvieilh 1990), Pat. No. 6,485,523 (Pierce et al 2002), Pat. No. 6,582,473 (Pierce et al 2003).

SUMMARY OF THE INVENTION

According to the present invention there is provided a prosthetic device for golfing which permits those who have had an upper extremity amputation, to use a golf club. The prosthetic device has an elongate resilient body with an axis, a first end, a second end and an exterior golf club support surface extending along the axis between the first end and the second end. Gripping members are positioned on opposed sides of the golf club support surface adjacent the first end. The gripping members are adapted to grip a golf club shaft and maintain the golf club shaft engaged with the golf club support surface. A coupling is provided at the first end which is adapted to be secured to a terminal device.

BRIEF DESCRIPTION OF THE DRAWINGS

These and other features of the invention will become more apparent from the following description in which reference is made to the appended drawings, the drawings are for the purpose of illustration only and are not intended to in any way limit the scope of the invention to the particular embodiment or embodiments shown, wherein.

DETAILED DESCRIPTION OF THE PREFERRED EMBODIMENT

Figure 1:
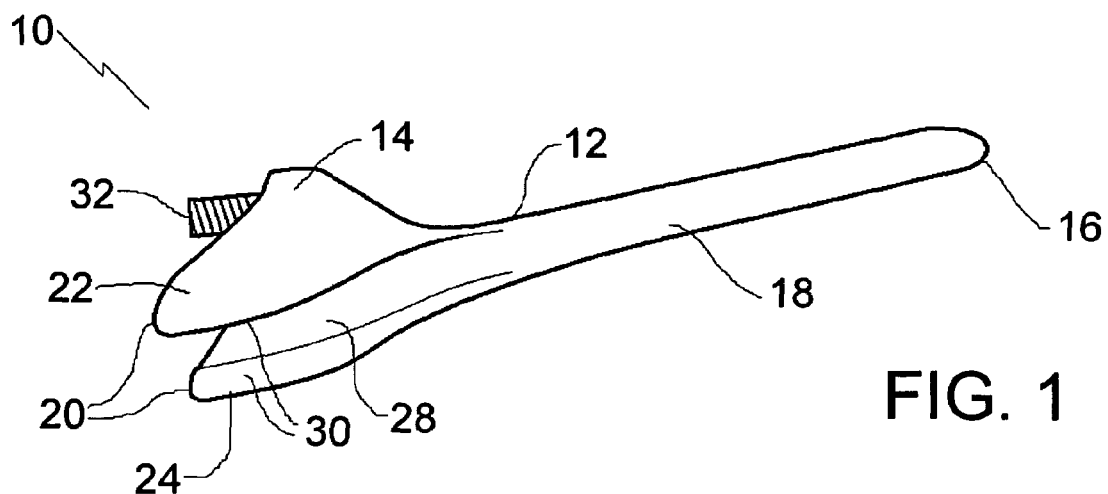
FIG. 1 is a perspective view of a prosthetic device for golfing.

The preferred embodiment, a prosthetic device for golfing generally identified by reference numeral 10, will now be described with reference to FIGS. 1 through 4.

Structure and Relationship of Parts:

Referring now to FIG. 1, there is shown prosthetic device 10 for golfing, including an elongate resilient body 12 that has an axis, a first end 14, a second end 16, and an exterior golf club support surface 18 extending along the axis between first end 14 and second end 16. As shown, second end 16 of resilient body 12 is parabolic in shape, and golf club support surface 18 is concave when viewed in transverse cross-section.

Figure 2:
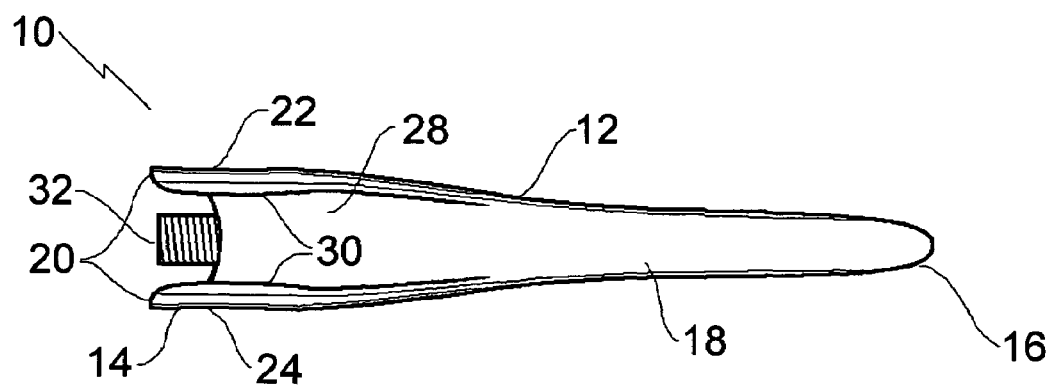
FIG. 2 is a bottom plan view of the prosthetic device for golfing as illustrated in FIG. 1.
Figure 3:
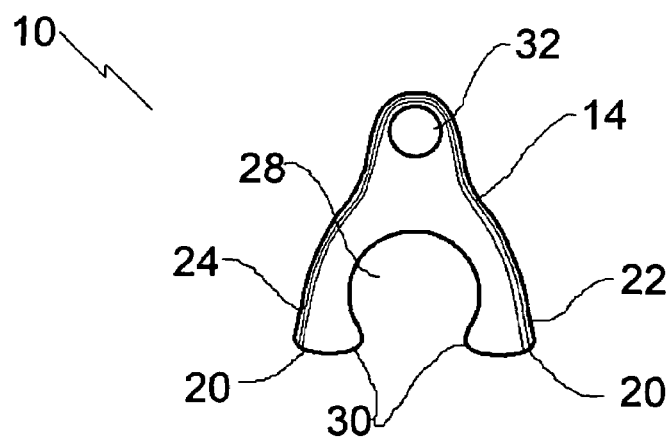
FIG. 3 is an end elevation view of the prosthetic device for golfing as illustrated in FIG. 1.
Figure 4:
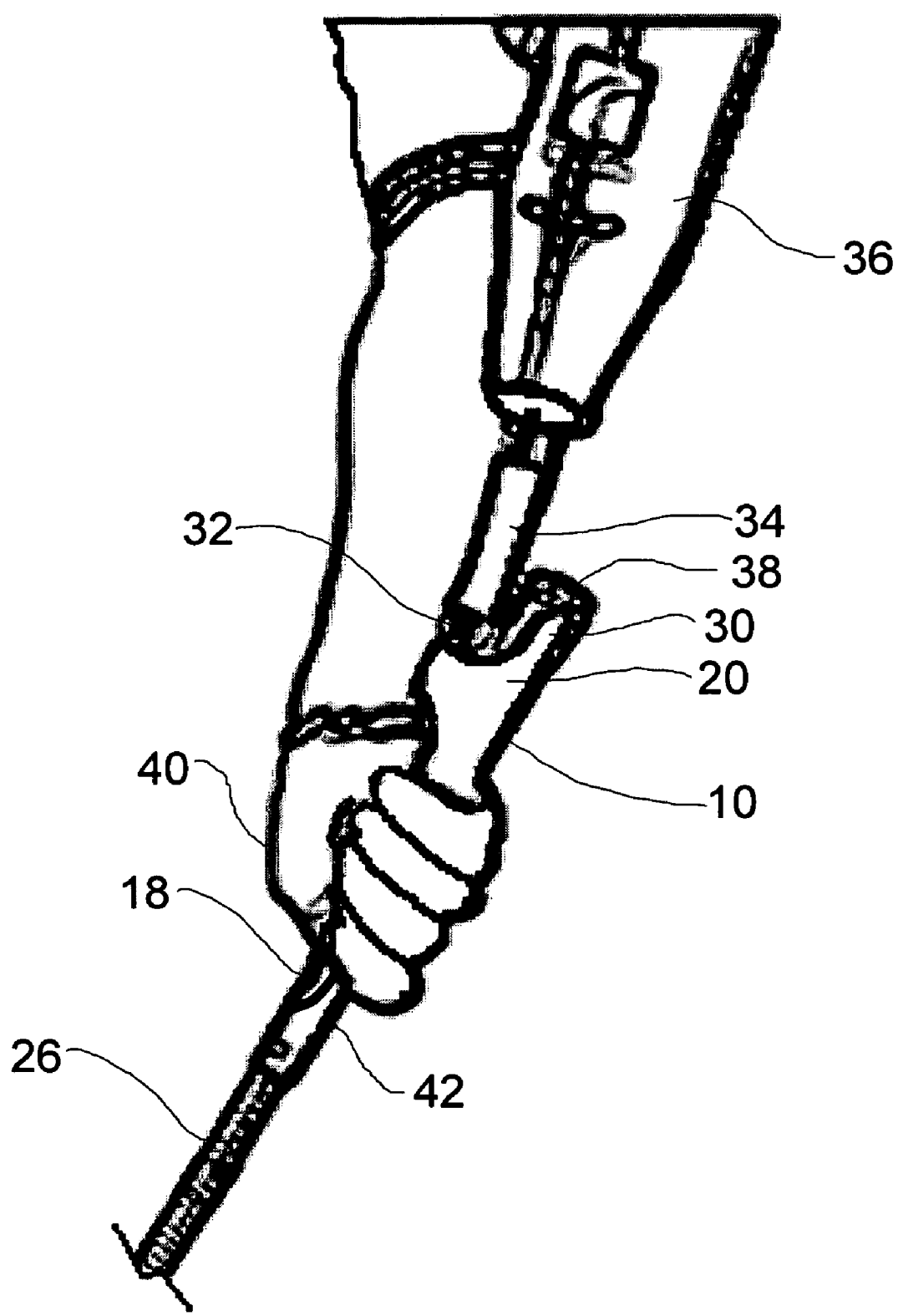
FIG. 4 is a side elevation view of the prosthetic device for golfing in use.

There are opposed gripping members 20 extending perpendicular to body 12 with one on each opposed side 22 and 24 of golf club support surface 18 adjacent to first end 14. Referring to FIG. 4, gripping members 20 are adapted to grip a golf club shaft 26 and maintain golf club shaft 26 engaged with golf club support surface 18. Referring to FIG. 3, gripping members 20 form a channel 28 which is generally C-shaped in cross-section to accommodate golf club shaft 26 (as shown in FIG. 4), and terminate in inwardly extending shoulders 30. Referring to FIG. 2, a male coupling element 32 protrudes axially from first end 14 that is adapted to be secured to a terminal device, such as a resilient member 34 attached to a prosthetic arm 36 as shown in FIG. 4.

Operation:

The use and operation of prosthetic device 10 for golfing will be discussed with reference to FIGS. 1 through 4. Referring to FIG. 1, prosthetic device 10 is provided as described above. Using coupling element 32, first end 14 is attached to resilient member 34, which is attached to prosthetic arm 36. Resilient member 34 of terminal device 36 can have differing lengths depending on the nature of the amputation. Typically, resilient member 34 made of high performance steel hydraulic hose. Golf club shaft 26 is then inserted into channel 28 and between gripping members 20, such that inwardly extending shoulders 30 are below the wider, upper portion 38 of golf club shaft 26. The space between shoulders 30 is designed to be wide enough to allow a narrower portion of shaft 26 to pass through, but not the wider portion 38 of shaft 26, allowing for a tight hold. Once upper portion 38 is secure, shaft 26 is then brought up to rest against golf club support surface 18, and is held their by the users hand 40, by applying force down on top of golf club support surface 18, and up on shaft 26. With user's hand 40 holding the club on the grip portion 42, and shoulders 30 holding the wider upper portion 38, the club is secured to allow the user to take a swing. Once the golf swing is complete, shaft 26 is easily removed from support surface 18 by reversing the procedure. It is envisaged that prosthetic device 10 can be used by either right handed or left handed golfers.

Figure 5:
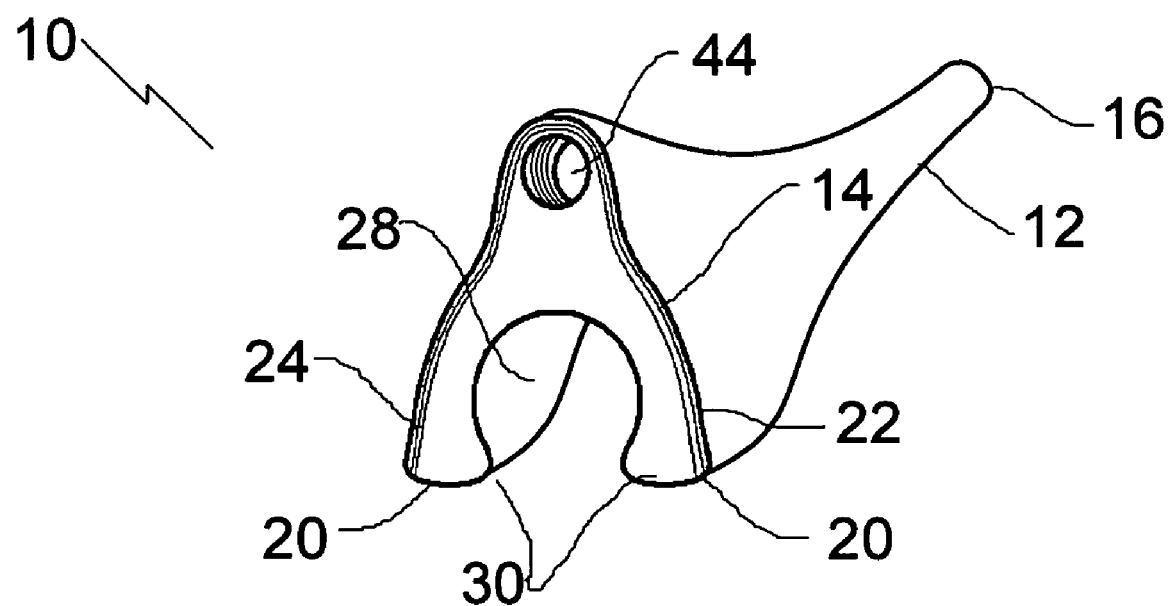
FIG. 5 is a end perspective view of a variation of the prosthetic device for golfing as illustrated in FIG. 1.

Variations:

It will be appreciated that although two gripping members 20 are illustrated in the preferred embodiment, there may be more than two gripping members. It will be appreciated that although second end 16 is parabolic in shape in the preferred embodiment, this is not essential to the operation of the invention. It will finally be appreciated that although a male coupling 32 is illustrated in the preferred embodiment, a female coupling can also be used to connect to the terminal device. Referring to FIG. 5, there is illustrated a female coupling 44. One way that female coupling 44 may be formed is by embedding a nut within body 12. If desired, the coupling can easily be changed from female back to male by threading a bolt into female coupling 44. Male and female couplings 32 and 44 have been chosen for illustration, as these are the most commonly used couplings used with prosthetics. It will be understood, however, that any suitable coupling could be used.

In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be one and only one of the elements.

It will be apparent to one skilled in the art that modifications may be made to the illustrated embodiment without departing from the spirit and scope of the invention as hereinafter defined in the Claims.

What is claimed is:

1. Prosthetic device for golfing, comprising;
   an elongate resilient body having an axis, a first end, a second end and a single exterior golf club support surface concave in cross-section extending along the axis between the first end and the second end;
   at least two opposed gripping members integrally formed with and extending outwardly from the body with at least one on each of opposed sides of the golf club support surface adjacent the first end, the at least two gripping members forming a channel co-axial with the golf club support surface which is generally C-shaped in cross-section to engage a golf club grip and prevent movement of the golf club grip in an axial direction;
   a majority of the golf club support surface being open to facilitate insertion of a golf club positioned parallel to the body and extending past the at least two gripping members toward the second end to provide support along the golf club grip and prevent lateral movement of the golf club grip when the golf club support surface and the golf club grip are gripped by a user's hand; and
   a coupling at the first end for securing the body to a terminal device.

2. The prosthetic device as described in claim 1, wherein the gripping members form a channel which is generally C-shaped in cross-section to accommodate a golf club shaft.

3. The prosthetic device as described in claim 1 wherein the gripping members terminate in inwardly extending shoulders.

4. The prosthetic device as described in claim 1, wherein the coupling is a male coupling.

5. The prosthetic device as described in claim 1, wherein the coupling is a female coupling.

6. Prosthetic device for golfing, comprising;
   an elongate resilient body having an axis, a first end, a second end and a single exterior golf club support surface concave in cross-section extending along the axis between the first end and the second end;
   two opposed gripping members integrally formed with and extending outwardly from the body with one on each of opposed sides of the golf club support surface adjacent the first end, the two gripping members forming a channel co-axial with the golf club support surface which is generally C-shaped in cross-section which engages a golf club grip and prevents movement of the golf club grip in an axial direction;
   a majority of the golf club support surface being open to facilitate insertion of a golf club positioned parallel to the body and extending past the at least two gripping members toward the second end to provide support along the golf club grip and prevent lateral movement of the golf club grip relative to the golf club support surface when the golf club support surface and the golf club grip are gripped by a user's hand; and
   one of a male coupling or a female coupling at the first end for securing the body to a terminal device.

7. The prosthetic device as described in claim 6, wherein the gripping members terminate in inwardly extending shoulders.

8. A prosthetic device for golfing, the prosthetic device comprising:
   an elongated resilient body having an axis, a first end, a second end, and a single exterior golf club support surface concave in cross-section extending along the axis between the first end and the second end;
   two opposed gripping members integrally formed with and extending outwardly from the body with one on each of opposed sides of the golf club support surface adjacent the first end, the two gripping members forming a channel co-axial with the golf club support surface which is generally C-shaped in cross-section for engaging a golf club grip and preventing movement of the golf club grip in an axial direction;
   a majority of the golf club support surface being open to facilitate insertion of a golf club positioned parallel to the body and extending past the at least two gripping members toward the second end provides axial support along the golf club grip and prevents movement of the golf club grip when a hand of a user directly grips both an exterior of the golf club support surface and the golf club without gripping either of the to opposed gripping members; and
   a coupling element, supported by the first end, facilitates coupling of the first end to a terminal device.

* * * * *